United States Patent [19]
Frankel

[11] Patent Number: 5,718,247
[45] Date of Patent: Feb. 17, 1998

[54] APPARATUS AND PROCESS FOR INTERACTIVE PSYCHOTHERAPY

[76] Inventor: Kenneth Frankel, P.O. Box 1351, Ross, Calif. 94957

[21] Appl. No.: 655,632

[22] Filed: May 30, 1996

[51] Int. Cl.$^6$ .................................................. A61B 19/00
[52] U.S. Cl. .................................................. 128/898
[58] Field of Search ........................... 434/236; 128/879, 128/898

[56] References Cited

U.S. PATENT DOCUMENTS 5,435,324  7/1995  Brill ..................................... 128/897

OTHER PUBLICATIONS

MacFarquhar, Larissa. "Point and click." The New Republic, 215(15): 14–15, Apr. 1996.
Jongsma, Arthur E. "TheraScribe" (Treatment planning software) Wiley and Sons Publishing, Oct. 1995.
Fligsten, Kenneth E. M.D. "Psychnosis" computer program, 1993.
Marcus, Steven. "The Clinical Practice Director" Software package by Computerized Psychological, 1993.
Jongsma, A.E. and L. Mark Peterson "The Complete Psychotherapy Treatment Planner." John Wiley & Sons Publishers, pp. 1–9+ Mar. 1995.
Hewlet Packard Patient Data Management System: System Description Model 78707A, Jan. 1982.

*Primary Examiner*—V. Millin
*Assistant Examiner*—Kelly R. O'Hara
*Attorney, Agent, or Firm*—Michael A. Glenn

[57] ABSTRACT

A process and apparatus for interactive psychotherapy in which information produced during a patient's therapy is categorized according to data type. The information is then stored to a series of interconnected databases stored in a computer. Empirical Data and Historical Data are developed first, and stored. Then Generalizations (patterns) are derived from this Data, and stored. After Generalizations have been stored, Hypotheses (Explanations of Generalizations) are developed and stored. The Hypotheses are evaluated and tested to determine their truth or falsity. Simultaneously with the derivation of Hypotheses, Goals are derived from the Generalizations, and stored. These Goals are periodically evaluated to assess the patient's progress. Finally, possible Actions to accomplish the Goals are Derived, each Action being based on a Hypothesis. The patient and therapist are provided with simultaneous access to the computer for entry and retrieval of information. The computer has a means of data entry and a means of display for both therapist and patient. Storage is provided for the databases. These databases are accessed jointly by the patient and therapist during the therapy sessions, as well as by the therapist before, during, or after therapy sessions, thereby promoting interactive psychotherapy.

18 Claims, 7 Drawing Sheets

FIG. 3A   /–300

Stage 1: Historical Data and Empirical Data are Entered

Historical Data *305*

> 1) Mary divorced her husband four years ago.
> 2) Mary had a short story published in a local magazine three years ago.
> 3) Mary was diagnosed as having severe depression 10 years ago. Her symptoms were loss of appetite, insomnia, and extreme feelings of sadness. These symptoms lasted for about two years.
> 4) Mary has been working as an executive at a computer software company for the last seven years.
> 5)...
> 6)...
> etc.

Empirical Data *310*

> 1) Mary just got a raise and promotion at work.
> 2) Mary has had almost no interest in food for the past three months.
> 3) Mary argued bitterly with her secretary at work today, over what she thinks was a trivial matter.
> 4) Mary has had a lot of difficulty falling asleep for the past three months.
> 5) Mary just had a short story she wrote accepted for publication by a local magazine.
> 6) Mary has been feeling extremely sad for the past three months, so much so that she has lost all interest in anything in her life.
> 7)...
> 8)...
> etc.

/–315
Stage 2: Generalizations are Derived   /–320
Part A: Historical Data and Empirical Data that Form a Pattern are Selected Historical Data *325*

> Mary was diagnosed as having severe depression 10 years ago. Her symptoms were loss of appetite, insomnia, and extreme feelings of sadness.

Empirical Data *330*

> 1) Mary has had almost no interest in food for the last week.
> 2) Mary has had a lot of difficulty falling asleep for the last week.
> 3) Mary has been feeling extremely sad for the last week, so much so that she has lost all interest in anything in her life.

↓ *335*

Part B: Generalization Statement is Formulated and Entered

Generalization *340*

> Mary is suffering from Depression at present.

↓ *345*

Stage 3: Goals and Hypotheses are Derived From Generalizations

Goal *350*

> Mary wants to alleviate her depression.

Hypotheses *355*

> 1) Mary is depressed because she has a biological or biochemical imbalance, that is, because of physical causes.
> 2) Mary is depressed because of guilt from rejecting her mother and father.
> 3) Mary is depressed because she and her husband argue constantly, and her marriage seems to be crumbling.

↓ *360*

Stage 4: Actions are Defived From Goals and Hypotheses

Potential Actions to Accomplish the Goal "Alleviate Mary's Depression" *365*

> 1) Mary should try taking anti-depressant medication, such as an SSRI. (This Action is based on Hypothesis #1).
> 2) Mary should go to a nutritionist, have her diet analyzed, and try eating a more healthy diet. (Another Action based on Hypothesis #1).
> 3) Mary should work in her therapy to understand and reduce her feelings of guilt. (Action based on Hypothesis #2).
> 4) Mary should try family therapy with her husband. (This Action is based on Hypothesis #3).

FIG. 3B

Empirical Data ╱─500
- Title ─ 501
- Date of Entry ─ 502
- Narrative Field ─ 503
- Opinion of Importance ─ 504
- Certainty of Reality of Occurrence ─ 505
- Number of Previous Occurrences ─ 506
- Concurrent Life Events ─ 507
- KeyWords ─ 508

Historical Data ╱─510
- Title ─ 511
- Date of Entry ─ 512
- Narrative Field ─ 513
- Opinion of Importance ─ 514
- Certainty of Reality of Occurrence ─ 515
- Age of First Occurrence ─ 516
- Age of Last Occurrence ─ 517
- Age of Major Impact on Life ─ 518
- KeyWords ─ 519

Generalizations ╱─520
- Title ─ 521
- Date of Entry ─ 522
- Narrative Field ─ 523
- Type of Generalization ─ 524
- Certainty of Reality of Occurrence ─ 525
- Opinion of Importance ─ 526
- KeyWords ─ 527

Hypotheses ╱─530
- Title ─ 531
- Date of Entry ─ 532
- Narrative Field ─ 533
- Title of Generalization Explained ─ 534
- Likelihood of Truth ─ 535
- KeyWords ─ 536

Goals ╱─540
- Title ─ 541
- Date of Entry ─ 542
- Narrative Field ─ 543
- Rating of Importance ─ 544
- Type or Status of Goal ─ 545
- Title of Generalization Derived From ─ 546
- KeyWords ─ 547

Evaluations of Hypotheses ╱─550
- Title of Hypothesis ─ 551
- Date of Evaluation ─ 552
- Method of Evaluation ─ 553
- Opinion of Truth of Hypothesis ─ 554
- Reasons for Opinion (narrative) ─ 555

Evaluations of Therapy Progress ╱─560
- Title of Goal Evaluated ─ 561
- Date of Evaluation ─ 562
- Rating of Accomplishment of Goal ─ 563
- Reasons for Rating (narrative) ─ 564

Actions to Accomplish Goals ╱─570
- Title of Action ─ 571
- Date of Entry ─ 572
- Description of Action (narrative) ─ 573
- Title of Goal to be Accomplished ─ 574
- Title of Hypothesis on Which Based ─ 575
- Likelihood of Action Accomplishing Goal ─ 576
- Rating of Importance ─ 577
- KeyWords ─ 578

Dreams ╱─580
- Title of Dream ─ 581
- Date of Dream ─ 582
- Patient's Associations (narrative) ─ 583
- Interpretations (narrative) ─ 584
- KeyWords ─ 585

List of Patients ╱─590
- Name ─ 591
- Date Therapy Started ─ 592
- Address ─ 593
- Telephone Numbers ─ 594
- etc...

Therapist Notes ╱─586
- Narrative Field ─ 587
- Date of Entry ─ 588

*FIG. 5*

APPARATUS AND PROCESS FOR INTERACTIVE PSYCHOTHERAPY

BACKGROUND OF THE INVENTION

1. TECHNICAL FIELD

The invention relates to psychotherapy. More particularly, the invention relates to an apparatus for interactive psychotherapy for simultaneous use in real time therapy by a patient and therapist.

2. DESCRIPTION OF THE PRIOR ART

In conventional psychotherapy, a patient and a therapist meet to discuss issues of concern. The therapist often takes notes during the therapy session and generates a report afterwards. In some cases, the therapist does not take notes, but writes a report after the session has concluded. Disorganized or incorrect notes may affect the accuracy of the therapist's report.

As the therapist must direct his/her attention to the patient, it is difficult to record all of the information from a therapy session. Furthermore, it is not possible to know when a statement made during a particular session will later generate a significant therapy issue.

The therapist, therefore, can either be delayed in discovery, or miss entirely an important problem of the patient. Furthermore, as memories fade with time, the patient and therapist may develop different recollections of earlier sessions. Misunderstandings and distortions of reality are thereby promoted.

It is known to use a computer to store patient information arising from psychotherapy. In Brill, Apparatus for Measuring Psychotherapy Outcomes, U.S. Pat. No. 5,435,324 (25 Jul., 1995), a computer is used to measure a patient's psychotherapy process. A questionnaire measuring psychological variables is administered to the patient to obtain initial information. Responses to the questionnaire are used to compute single-valued quantities as psychological measures of the patient. Computed scores from subsequent therapy sessions are then compared to quantify the patient's progress.

The apparatus and method of Brill are specifically for use by the therapist only. No provision is made for the patient to use the computer at any time. The patient is thus not participating at a very active level in his/her therapy. The therapist-patient power dynamic developed during some prior art therapy can often impair the therapeutic process.

Brill is directed to quantifying a patient's psychological condition with a score. This is a subjective process, and is dependent upon many variables such as the patient's educational level, cultural background, level of honesty, or the therapist's feelings towards the patient.

Not all psychological conditions are quantifiable in such manner. Furthermore, assigning a score to a patient's condition may actually produce significant feelings of anxiety in the patient, and be a detriment to the therapeutic progress.

Brill does not address problems such as misunderstandings and distortion of reality. The method does not assist in the discovery of new issues requiring treatment.

It would therefore be advantageous to provide a process and apparatus that increases the accuracy of the information obtained during psychotherapy. It would be a further advantage if this information were readily available to organize the therapy process, minimize misunderstandings and distortions of reality, and promote the development of goals and actions for the patient. It would be yet a further advantage if such process and apparatus were adapted to permit simultaneous use by both patient and therapist.

SUMMARY OF THE INVENTION

The invention provides a process and apparatus for interactive psychotherapy. Information produced during a patient's therapy is categorized according to data type. The information is then stored to a series of interconnected databases stored in the computer. Empirical Data and Historical Data are developed first, and stored. Then Generalizations (patterns) are derived from this Data, and stored. After Generalizations have been stored, Hypotheses (Explanations of Generalizations) are developed and stored. The Hypotheses are evaluated and tested to determine their truth or falsity. Simultaneously with the derivation of Hypotheses, Goals are derived from the Generalizations, and stored. These Goals are periodically evaluated to assess the patient's progress. Finally, possible Actions to accomplish the Goals are Derived, each Action being based on a Hypothesis.

The apparatus of the invention provides patient and therapist with simultaneous access to the computer for entry and retrieval of information. The computer has a means of data entry and a means of display for both therapist and patient. Storage means are provided for the databases. These databases are accessed jointly by the patient and therapist during the therapy sessions, as well as by the therapist before, during or after therapy sessions, thereby promoting interactive psychotherapy.

BRIEF DESCRIPTION OF THE DRAWINGS

FIG. 3A is an example of the process shown in FIG. 2;

FIG. 3B is an example of the process shown in FIG. 2;

FIG. 5 is a chart showing the databases used in the preferred embodiment of the invention;

DETAILED DESCRIPTION OF THE INVENTION

Figure 1:
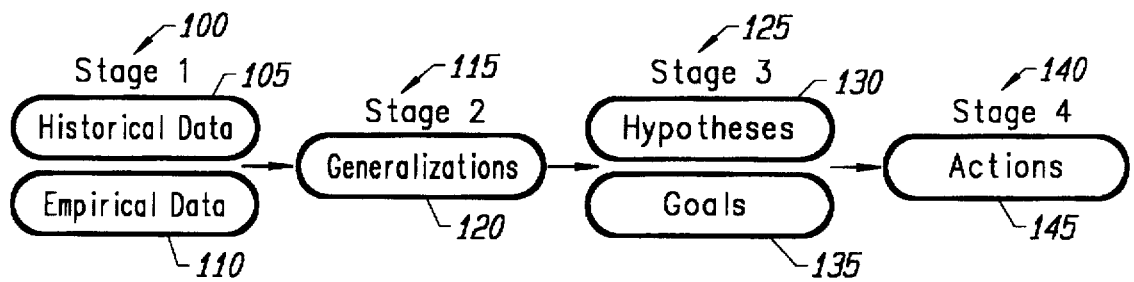
FIG. 1 is flow chart of an interactive psychotherapy system, including a four stage process according to the invention.

In this invention, an interactive psychotherapy system is implemented in four stages. Each stage depends on the preceding stage. FIG. 1 is flow chart of this process.

Stage 1 (100) is the development of Historical Data (105) and Empirical Data (110).

Stage 2 (115) is the derivation of Generalizations (120) from the information developed in Stage 1.

Stage 3 (125) is the derivation of Hypotheses (130) to explain the Generalizations, and simultaneously the derivation of Goals (135) based on the Generalizations. At the same time, as part of Stage 3, the Hypotheses are tested and evaluated to determine ideas about their truth or falsity.

Stage 4 (140) is the derivation of Actions (145) to accomplish the Goals. Each Action is specific to the Goal it is meant to accomplish, and is also based upon a particular Hypothesis.

Figure 2:
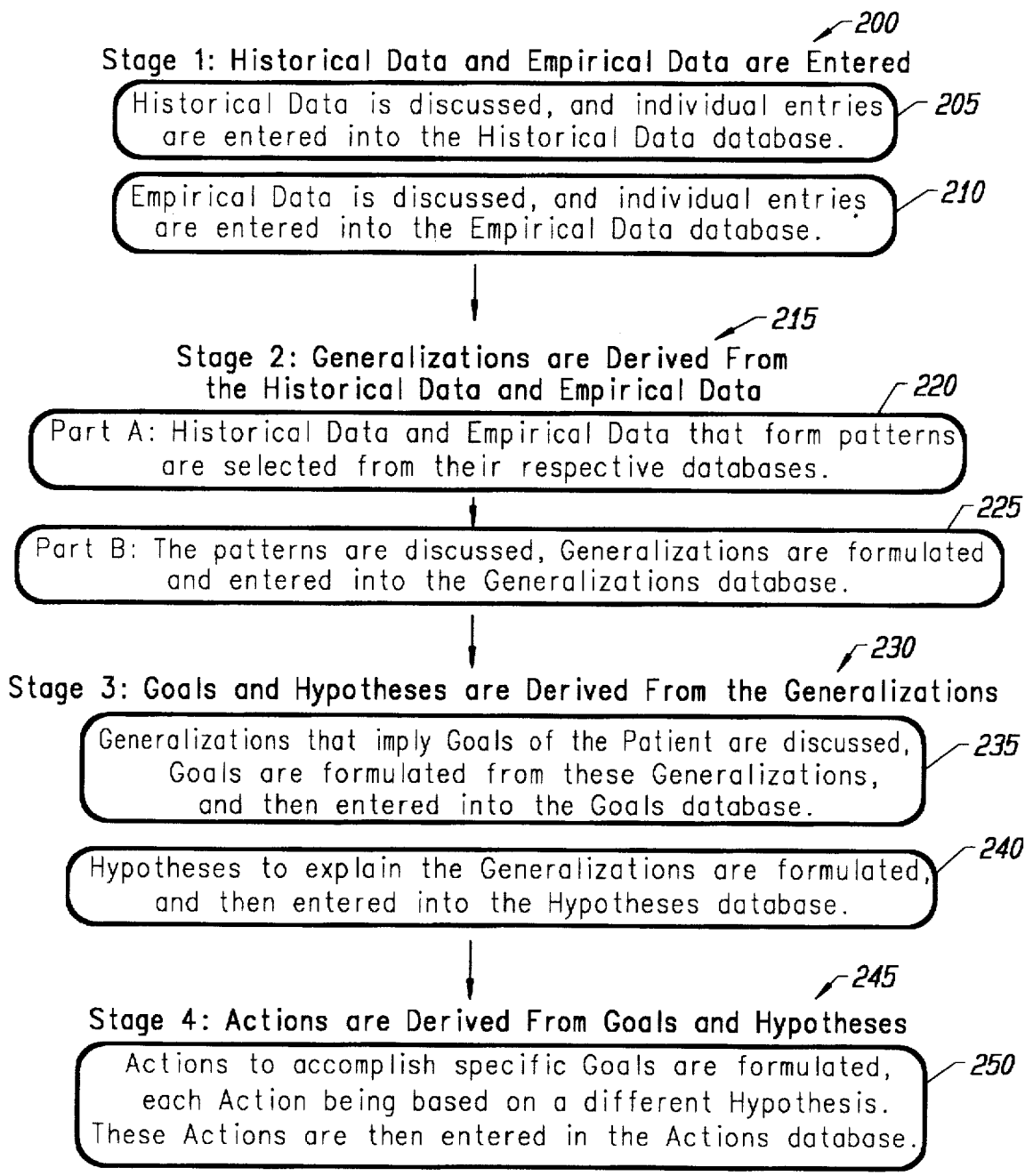
FIG. 2 is a flow chart showing the four-stage process of FIG. 1 in more detail.

FIG. 2 is a flow chart demonstrating this four-stage process in more detail.

Stage 1 (200): Empirical Data and Historical Data are developed and stored in the computer Historical Data (205) is information about past occurrences in the patient's life. For example "John's father got drunk and yelled at John often when John was a 8–10 year old" is Historical Data (if John is in therapy as an adult). The therapist and patient discuss the patient's history, and historical data that seems important enough to enter is entered in the Historical Data database.

Empirical Data (210) are any specific pieces of information, or specific statements of things that happened. Some examples of Empirical Data are: "Mary yelled at her secretary today", and "John is feeling depressed today", and "Mary divorced her husband last week" (too recent to be Historical Data). The therapist and patient discuss the patient's life in general, and any information that isn't historical that seems important enough to record is entered in the Empirical Data database.

Stage 2 (215): Generalizations are derived from the Empirical Data and Historical Data, and stored Generalizations state patterns made by Empirical Data and/or Historical Data. For example "John feels depressed every Monday that he has to work, and on no other days". Since they are more general, their accuracy is not as certain as the accuracy of Empirical Data and Historical Data. However, a Generalization is often a discovery of new information about a patient, that is, discovery of a pattern that wasn't known to the patient before therapy. In Part A (220) of Stage 2, the previously entered Empirical Data and Historical Data is examined and discussed, with the intent of discovering patterns. When a pattern is discovered, in Part B (225) of Stage 2, the pattern is discussed and formulated as a Generalization, and entered into the Generalizations database. If the therapy stops during Stage 2, without going on to subsequent stages, it will still be a successful use of this invention, as new information will have been developed that wasn't know before. This should at least help the patient understand himself/herself better, and the information will be in the computer for future use if therapy restarts, even with a different therapist.

Stage 3: Goals and Hypotheses are derived from the Generalizations, and stored (230)

Goals are the patient's life goals. They can be long term goals, such as "Be fulfilled in my career", or short term goals such as "Reduce the anger I display toward my employees". They can also include therapy goals, such as "Learn to understand the reasons for my anger". As part of Stage 3, Goals are derived from Generalizations (235). Any Goal a patient has is based on a related Generalization. In this invention, the Generalization is entered first, and the Goal then derived from it. For example, the Goal "Be fulfilled in my career" might be based on the Generalization "Mary is not feeling fulfilled by her job".

Hypotheses are hypothetical explanations of Generalizations. Every Generalization can have many possible explanations. These could be explanations of psychological reasons for the situation described in the generalization, or they could be practical reasons with little psychological overtone. For example, a few Hypotheses of why John is depressed on Mondays could be "John hates his job and feels this most on Mondays", "John takes sleeping pills to get to sleep every Sunday night, and these make him depressed", and "John's father died of a heart attack while working late on a Monday". Hypotheses include any reasonable idea of the therapist's or patient's to try to explain a Generalization. As this part of Stage 3 (240), possible explanations of the Generalizations are discussed, and ones that seem reasonable or have some likelihood of being true are entered in the Hypotheses database. Once stored, Hypotheses may be tested to determine the extent of their truth or falsity.

It is not necessary to go on to Stage 4. The derivation, testing, and rating (of truth or falsity) of Hypotheses is a very successful use of this invention. It is much more than is done in psychotherapy at present. The derivation and explicit statement of Goals is also a very successful use of this invention.

Stage 4: Actions to Accomplish Goals are derived from the Goals and Hypotheses, and stored (245)

A Goal usually has several possible Actions that might accomplish it. Each Action is based on a different Hypothesis. Since every Goal is based on a Generalization, the Hypotheses used to derive Actions to accomplish that Goal would be the Hypotheses to explain the Generalization the Goal is based on. In other words, a particular Generalization might lead to a Goal, and several Hypotheses to explain it. Each Hypothesis would then generate a different Action to accomplish the Goal. In Stage 4, the Goals are discussed, and for each Goal, the various related Hypotheses (Hypotheses to explain the Generalization the Goal is based on) are examined and discussed. Then (250), Actions to accomplish the Goal are formulated, each Action being based on a different Hypothesis, and the Actions are then entered in the Actions database.

FIG. 3A and 3B is an example of the process described in FIG. 2. In this figure, one area from the therapy of Mary is analyzed according to the system of this invention. The area demonstrated in FIG. 3 is Mary's depression.

Stage 1. The first step is to discuss, and then enter into the computer, Historical Data and Empirical Data (300). In this example, several Historical Data entries are stored in Mary's Historical Data database 305). Four of these entries are listed here. In addition, several Empirical Data entries are stored in Mary's Empirical Data database (310). Six of these entries are listed here. At this point, the data is not organized or selected by the therapist or patient, except in being selected as important enough to record.

Stage 2. The second step in this invention is to derive Generalizations (315) from the Historical Data and Empirical Data that have been previously entered. In Part A (320) of Stage 2, Mary's Historical Data and Empirical Data is discussed by the therapist and Mary. It is noticed that several entries form a pattern. The Historical Data entry that is part of the pattern (325) relates to Mary's past history of depression. The Empirical Data entries that are part of the pattern (330) relate to Mary's current symptoms. In Part B (335) of Stage 2, this pattern is discussed, and then formulated as the Generalization "Mary is suffering from depression at present", and stored into the Generalizations database (340).

Stage 3. In this stage (345), Goals and Hypotheses are derived from the Generalization that has just been entered. The Goal (350) is obvious: Mary wants to alleviate her depression. The Hypotheses (355) are all the reasonable possible explanations of why Mary is depressed. Three Hypotheses are listed here. The first ("biological imbalance") is a physical explanation. The second ("guilt") is a psychological reason. The third (problems in her marriage) is a practical reason. There could be several other possible reasons. Once these Hypotheses are derived and entered in the computer, they should be tested. Methods of testing Hypotheses are discussed later.

Stage 4. In the last stage (360), Actions are derived from the Goal and the Hypotheses that have just been entered in the computer. In this example, four different Actions that might accomplish the Goal "alleviate depression" are derived and entered. As shown, the first two Actions are based on the Hypotheses about biological imbalance. The next Action is based on the Hypothesis about guilt, and the last Action is based on the Hypothesis about problems in Mary's marriage. (As can be seen, a Hypothesis can generate more than one Action to accomplish a particular Goal).

Figure 4:
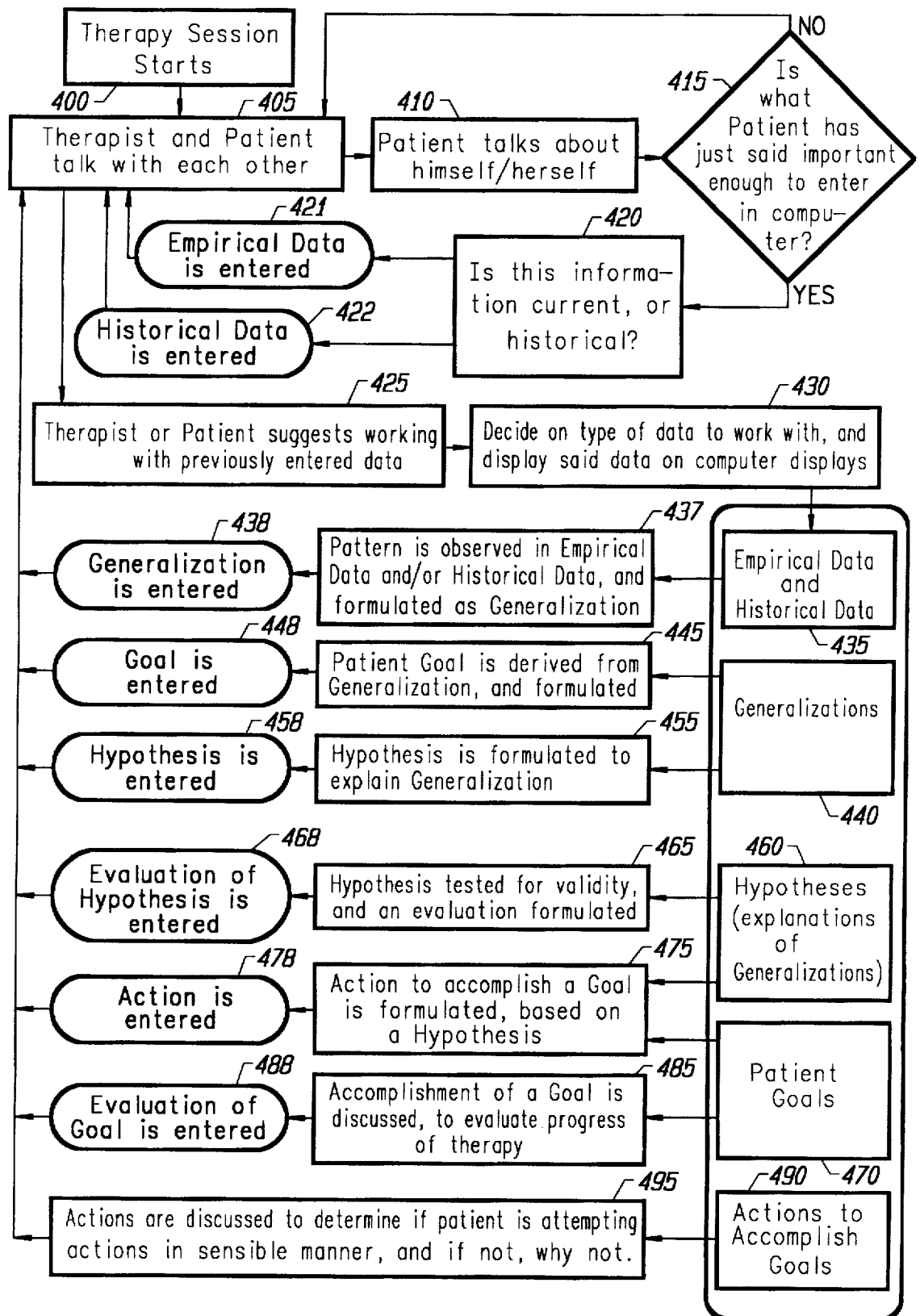
FIG. 4 is a flow chart showing how a psychotherapy session is conducted according to the invention.

FIG. 4 is a flow chart demonstrating how a psychotherapy session is conducted according to this invention. As a therapy session starts (400), the patient and psychotherapist talk with each other(405).

During part of the therapy session, the patient talks about himself/herself (410), as is common in all talk psychotherapy. As the patient talks, the therapist makes a determination whether what the patient has said is important enough to enter into the computer. If not, the talk therapy proceeds. If the information is of sufficient importance to store, a decision is made as to whether the information is current or historical(420). If the information is current, it is entered into the computer as Empirical Data (421). If the information is historical, it is entered into the computer as Historical Data (422). After the data is entered, the patient and therapist continue talking with each other (405).

During another part of the therapy session, the therapist might want to work with previously entered data (425). If this is to be done, the therapist decides on which type of previously entered data to work with, and then displays this data on the computer screens (430). After looking at the data, a decision may be made to enter new data, based on the data being examined. The type of new data derived from each type of previously entered data is described below. However, it is also possible that no new data may be entered. The patient and therapist may just discuss the displayed data and its implications, which might bring up other issues, thoughts, feelings, memories, etc., and the patient and therapist then go back to the stage of talking with each other (405).

If the data displayed is Empirical Data or Historical Data (435), a pattern may be observed in the data. If so, this pattern should be formulated as a Generalization (437). This Generalization should then be entered into the computer (438). The therapy session would then continue with the patient and therapist talking with each other (405).

If the data displayed is Generalizations (440), these can lead to the formulation of two different types of data. First, a patient Goal may be derived from a Generalization (445). If this is done, the Goal should be formulated, and then entered into the computer (448). In the preferred embodiment of this invention, this Goal is given a numerical rating of its relative importance compared to the other patient Goals. Then the therapy would continue with the patient and therapist talking with each other (405). Another possibility is that the therapist would proposed a possible explanation for the Generalization. This would be formulated as a Hypothesis (455). In the preferred embodiment of this invention, this Hypothesis is given a numerical rating of the extent to which the therapist and patient believe it is true. This Hypothesis would then be entered into the computer (458), and the therapy would continue with the patient and therapist talking with each other (405).

If the data displayed is Hypotheses (460), the therapist might propose that a Hypothesis be evaluated for validity. A Hypothesis can be tested by many different methods, such as obtaining an outside opinion or consultation, looking at other previously entered data for confirmation, periodically obtaining the patients intuitive opinions, comparing the Hypothesis with the patient's dreams, or with any other method that the therapist and/or patient can think of. The Hypothesis would then be evaluated (tested) by the method selected, and an Evaluation of Hypothesis formulated (465). This Evaluation of Hypothesis would then be entered into the computer (468), and the therapy would continue with the patient and therapist talking with each other (405).

If the data displayed is patient Goals (470), these can lead to the formulation of an Action to accomplish one of said Goals. If this is to be done, a Goal would be selected, and then the Hypotheses would be displayed, in order to select which Hypothesis the Action is to be based on. After a Hypothesis was selected, the Action to accomplish the selected Goal would be formulated (475), based on the selected Hypothesis. In the preferred embodiment of this invention, this Action is given a numerical rating of importance, based on the a combination of the rating of importance of the selected Goal, the rating of the selected Hypothesis of the extent to which the therapist and patient believe it is true, and a rating of the likelihood of this Action accomplishing the selected Goal, assuming the selected Hypothesis is true. This Action would then be entered into the computer (478), and the therapy would continue with the patient and therapist talking with each other (405).

If the data displayed is patient Goals (470), another possibility is that the therapist might decide to evaluate the progress of the therapy by analyzing to what extent a particular Goal has been accomplished. In this case, the patient and therapist would discuss the accomplishment of the selected Goal, and an Evaluation of Goal would be formulated (485), said Evaluation containing a rating of the extent to which the Goal had been accomplished. This Evaluation of Goal would then be entered into the computer (488), and the therapy would continue with the patient and therapist talking with each other (405).

If the data displayed is Actions to Accomplish Goals, there is no higher lever of data that can be derived. The patient and therapist can discuss what the patient is doing in his/her life to proceed with the listed Actions, whether or not the patient is attempting the Actions, if so, whether with or without success, and if not, why not. If the Actions have been rated in importance by some method (such as the method described above), the patient's life in general can be discussed as to whether he/she is devoting time and energy to the Actions in accordance with their importance, and if not, why not. These discussions can lead to new insights and information, which may be important to the therapy, and may even lead to modifications being made in other previously entered data. After discussing the Actions, the therapy would continue with the patient and therapist talking with each other (405).

In the above described embodiment of this invention, all decisions of data type, importance of data, what data to enter, etc. are described as made by the therapist. In another embodiment of this invention, these decisions would be made jointly by the therapist and patient, as the patient has access to all the data jointly with the therapist.

FIG. 5 is a chart showing the databases (sometimes also called "tables") used in the preferred embodiment of this invention. Fields of each database used in one embodiment of this invention are also shown. It will be readily appreciated by one skilled in the art that other database configurations and other fields may be used without departing from the scope and spirit of the invention.

The Empirical Data database (500) is a collection of individual entries of current occurrences, feelings, thoughts, or other information concerning the patient's life. Each entry contains a field for a title for the entry (501) and a field for the date of the entry (502). The narrative field (503) is a statement that narrates the entry, i.e., describes the content of the entry. There are fields for numeric ratings of both the therapist's and the patient's opinion of the importance of the entry (504). There are fields for numeric ratings of both the therapist's and the patient's level of certainty that the occurrence described actually did occur (505). There is a field for the number of previous times the occurrence described has happened in the patient's life (506). There are one or more fields for a list of what else is occurring in the patient's life at the time of the entry (507). There are one or more fields to contain a list of keywords (508) that the therapist and/or patient associate with the entry.

The Historical Data database (510) is a collection of individual entries of historical events, occurrences, feelings, thoughts, or other information that occurred in the past in the patient's life. Each entry contains a field for a title for the entry (511) and a field for the date of the entry (512). The narrative field (513) is a statement that narrates the entry, i.e., describes the event or occurrence. There are fields for numeric ratings of both the therapist's and the patient's opinion of the importance of the event or occurrence (514). There are fields for numeric ratings of both the therapist's and the patient's level of certainty that the event described actually did occur (515). There is a field for the patient's age at which the event first occurred (516) and a field for the age at which it last occurred (517). There is a field for the patient's age at which the event had the most impact on his/her life (518). There are one or more fields to contain a list of keywords (519) that the therapist and/or patient associate with the entry.

The Generalizations database (520) is a collection of individual entries of patterns observed in the Historical Data and/or Empirical Data. Each entry contains a field for a title for the entry (521) and a field for the date of the entry (522). The narrative field (523) is a statement that describes the pattern that was observed. There is a field for the type of Generalization (524). In one embodiment of this invention, the types can be either "Informational", "Problem", or "Symptom of Problem". There are fields for numeric ratings of both the therapist's and the patient's level of certainty that the pattern described really does exist ("Certainty of Reality of Occurrence") (525). There are fields for numeric ratings of both the therapist's and the patient's opinion of the importance of the pattern described (526). There are one or more fields to contain a list of keywords (527) that the therapist and/or patient associate with the entry.

The Hypotheses database (530) is a collection of individual entries of proposed explanations of Generalizations. Each entry contains a field for a title for the explanation (531) and a field for the date of the entry (532). The narrative field (533) is a statement of the proposed explanation. There is a field for the title of the Generalization (534) that the entry attempts to explain. There are fields for numeric ratings of both the therapist's and the patient's opinions of the validity of the explanation, i.e., their certainty that it is true or correct ("Likelihood of Truth") (535). There are one or more fields to contain a list of keywords (536) that the therapist and/or patient associate with the entry.

The Evaluations of Hypotheses database (550) is a collection of individual entries of evaluations of previously entered Hypotheses that attempt to determine the validity or truth of the Hypotheses. Each entry contains a field for the title of the Hypothesis being evaluated (551), and a field for the date of the evaluation (532). There is a field for the type or method of evaluation (553). In one embodiment of this invention, these types can be either "Using Previously Entered Data", "Using an Outside Consultant", or "Other Therapeutic Method". There are fields for numerical ratings of the evaluators' opinions of tho validity of tho Hypothosis (554) and for tho reasons for these opinions (narrative fields) (555).

The Goals database (540) is a collection of individual entries, each of which is a separate goal of the patient's. Each entry contains a field for the title of the Goal (541), and a field for the date the Goal was entered into the computer (542). There is a narrative field in which the Goal is described (543). There is a numeric field in which the importance of the Goal is rated relative to the other patient Goals (544). There is a field for the type or status of the Goal (545). In one embodiment of this invention, these types of Goals may be either "Long-Term Active", "Short-Term Active", "Accomplished", "Temporarily Suspended", or "Abandoned". There is a field for the title of the Generalization from which the Goal was derived (546). There are one or more fields to contain a list of keywords (547) that the therapist and/or patient associate with the Goal.

The Evaluations of Therapy Progress database (560) is a collection of entries, each of which evaluates the extent to which a selected Goal has been accomplished on the date of the entry. Each entry contains a field for the title of the Goal being evaluated (561), and a field for the date of evaluation (562). There is a field for a numeric rating of the degree to which the Goal has been accomplished (563), and there is a narrative field that described the reason for that rating (564).

The Actions database (570) is a collection of entries, each of which describes a possible action to accomplish a selected Goal. Each entry contains a field for the title of the Action (571), and a field for the date of entry (572). There is a narrative field in which the Action is described in detail (573). There is a field for the title of the Goal to be accomplished. In addition, every Action is based on a particular Hypothesis, and there is a field in each entry for the title of the Hypothesis the Action is based on (575). There is a field for a numeric rating of the likelihood of the Action accomplishing the Goal (576), assuming that the Hypothesis the Action is based on is true. There is a field for a numeric rating of the importance of the Action for the patient's life (577). In one embodiment of this invention, this importance (577) is calculated by adding together equally weighted values of the importance of the Goal (544), the certainty of truth of the base Hypothesis (554), and the likelihood of success of the Action (576). Finally, there are one or more fields to contain a list of keywords (578) that the therapist and/or patient associate with the Action.

The Dreams database (580) is a collection of descriptions of the patient's dreams. Each entry contains a field for the title of the Dream (581), and a field for the date of the Dream (582). There is a narrative field for a description of the patient's associations to the dream (feelings or thoughts connected to the Dream) (583). There are narrative fields for both the patient's and the therapist's interpretation of the Dream (584). Finally, there are one or more fields to contain a list of keywords (585) that the therapist and/or patient associate with the Dream.

The Therapist Notes database (586) is a collection of records or entries, each entry of which contains the therapist's notes for a separate therapy session. This Notes database may be used to replace the usual handwritten therapist notes, and/or for information that the therapist and/or patient wants to store that doesn't belong in any of the other databases. Each entry has a narrative field which contains the body of the notes (587), and a field for the date of the entry (588).

In the preferred embodiment of this invention, there is a separate collection of these databases for each patient. For the system as a whole, there is also a database for Patient Information (590), which is essentially a list of the patients using the invention with the therapist, plus information about each patient. There is one entry or record for each patient. Each record has a fields for the patient's name (591), date therapy started (592), address (593), telephone numbers (594), social security number, family information, health insurance information, employment information, medical information, etc.

Figure 6:
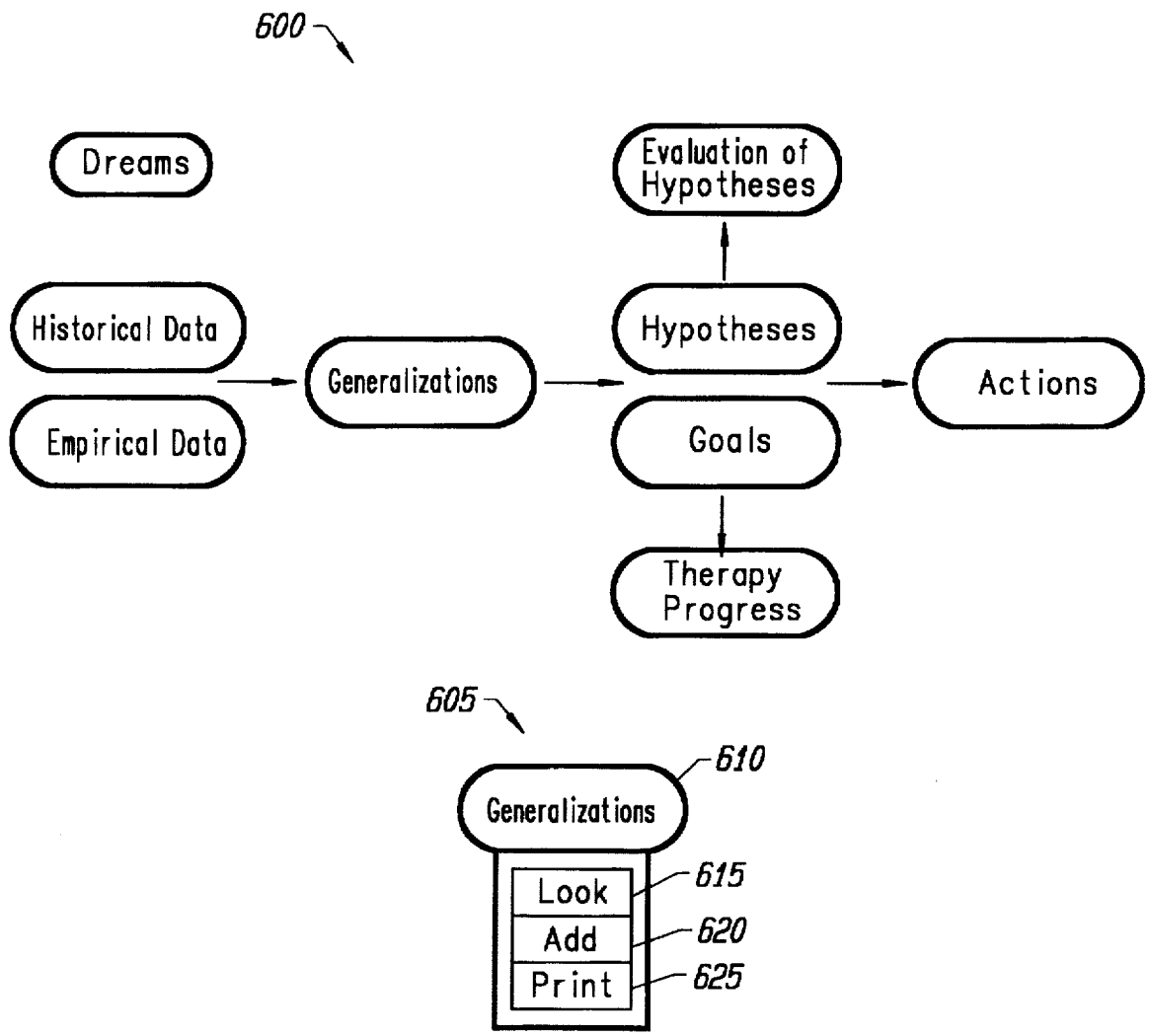
FIG. 6 shows how the main menu of the computer program works for one embodiment of the invention.

FIG. 6 shows how the main menu of the computer program works for one embodiment of this invention. The major part of the main menu consists of several ovals with the names of databases in the center (600), and arrows connecting the ovals showing the order of derivation of the data. When the mouse pointer is moved over any of the ovals, a drop-down (or drop-up) menu attached to that oval becomes visible, which menu gives the choices for that database. An example of a typical drop-down menu is given for the database Generalizations (605). In this example, when the mouse pointer is moved over the Generalizations oval (610), the drop-down menu below it appears. The users then have a choice to "Look" at previously entered Generalizations (615), "Add" a new Generalization (620), or "Print" a Generalization report (625), which choices are activated by clicking the square containing the appropriate word. For each of the databases, the users thus have a choice to look at previous data, add new data, or print reports. Various types of reports printed for each type of data. Examples of such reports include a list of Empirical Data indexed by date, a list of Historical Data indexed by date of major impact, a list of alternate Hypotheses to explain a selected Generalization, and a list of all Actions in order of importance.

Figure 7:
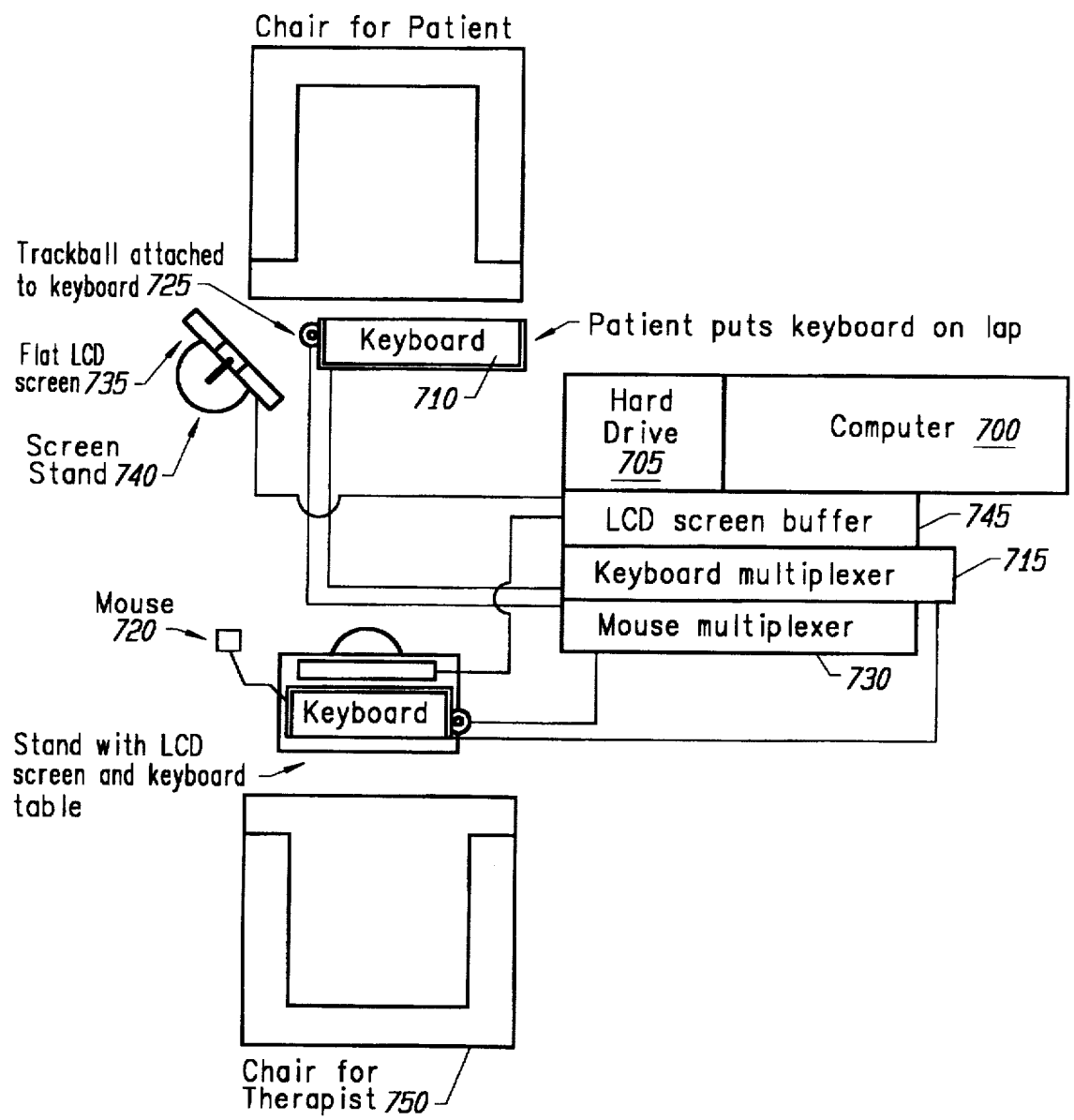
FIG. 7 is a diagram of the apparatus of the invention.

The apparatus of the invention is shown in the diagram of FIG. 7. The preferred embodiment of the invention includes a computer (700) for running the computer program. Storage means such as a hard drive (705), tape, cartridge or disk drives are required for the database storage.

In one embodiment of the invention, a personal computer is used. In alternate embodiments, a "dumb terminal" connected to a server retrieves the computer program using software such as "Java", developed by Sun Microsystems of Menlo Park, Calif. In yet another embodiment, at least one personal computer is connected to a central server.

Data entry means are provided for both patient and therapist to work alternately or simultaneously. Therefore, the patient and the therapist can both participate in making database entries. In the preferred embodiment of the invention, two keyboards (710) are connected to the computer by means of a keyboard multiplexer (715), such as that produced by Vetra Corporation of Plainview, N.Y.

Two pointing devices with a system for both to work simultaneously are also used in the preferred embodiment of the invention. These pointing devices include a mouse (720) or a trackball (725). A mouse multiplexer (730), such as the "Y-Mouse" produced by P.I. Engineering, Inc. of Williamston, Mich. may be used to connect more than one pointing device to the computer.

Display means are provided to permit both the patient and therapist to simultaneously see the computer display. In the preferred embodiment of the invention, the display is a computer monitor for conventional video display. The video display is configured differently in alternate embodiments of the invention.

In a first preferred embodiment, two individual displays are provided, one each for therapist and patient. Flat screens (LCD displays) (735) are preferred, as they take up less room in the therapy office. Each screen may be provided with a supporting stand (740). As LCD screens currently require a LCD video driver, they are interfaced with an electronic buffer (745), so both will function simultaneously.

In a second, equally preferred embodiment, projection video is used. In a third, equally preferred embodiment, a large screen monitor is arranged for both patient and therapist to view simultaneously. Chairs (750) are provided for the comfort of the therapist and patient during the session.

Although the invention is described herein with reference to the preferred embodiment, one skilled in the art will readily appreciate that other applications may be substituted for those set forth herein without departing from the spirit and scope of the present invention. For example, the invention is readily adapted for use in group therapy. The invention can be used with more than one therapist as well as with more than one patient. Telecommunication means can be joined to the apparatus. The invention can thus be used for "remote" therapy, where therapist and patient are not in the same room, such as through videoconferencing or the Internet.

The computer program according to the invention includes a method to add records to each of the databases, as well as various ways to look at, edit, or delete records previously added. The program may be provided with graphical or art modules. Thus, in alternate embodiments of the invention, the patient's progress is shown with graphs or other visual representations.

The data entry means can include means such as standard keyboards, voice-recognition and touch sensitive screens. The display may include a computer monitor, a projector and screen, or a television interconnected to the apparatus. Alternately, aural means such as a speaker may be provided for sight-impaired users.

Accordingly, the invention should only be limited by the Claims included below.

I claim:

1. A computer assisted process for interactive psychotherapy, comprising the steps of:

obtaining Empirical Data and Historical Data of a patient;

providing a computer database comprising a plurality of interrelated sub-databases;

entering said Empirical Data and Historical Data into said computer database;

accessing said computer database to display said Empirical Data and Historical Data;

sorting, manipulating, and examining said Empirical Data and Historical Data in said computer database to identify patterns therein;

developing Generalizations based on observed patterns in said Empirical Data and/or Historical Data;

entering said Generalizations into said computer database;

providing a plurality of input/output devices for said computer to access said computer database; and having said patient and a therapist simultaneously access said computer database via said input/output devices during a psychotherapy session.

2. The process of claim 1, further comprising the steps of:

accessing said computer database to display said Generalizations;

sorting, manipulating, and examining said Generalizations to develop Hypotheses to explain said Generalizations;

entering said Hypotheses into said computer database;

wherein said patient and said therapist may simultaneously access said computer database during psychotherapy.

3. The process of claim 2, further comprising the steps of:

accessing said computer database to display said Generalizations;

sorting, manipulating, and examining said Generalizations to develop specific patient Goals from said Generalizations; and entering said Goals into said computer database;

wherein said patient and said therapist may simultaneously access said computer database during psychotherapy.

4. The process of claim 3, further comprising the steps of:

displaying said Hypotheses and said patient Goals;

sorting, manipulating, and examining said Hypothesis and said Goals to develop Actions based upon said Hypotheses to accomplish said patient Goals; and entering said Actions into said computer database;

wherein said patient and said therapist may simultaneously access said computer database during psychotherapy.

5. The process of claim 3, further comprising the steps of:

accessing said computer database to display said Goals;

sorting, manipulating, and examining said Goals to evaluate to what extent said patient Goals have been accomplished; and entering said Evaluations of Goals into said computer database;

wherein said patient and said therapist may simultaneously access said computer database during psychotherapy.

6. The process of claim 2, further comprising the steps of:

evaluating said Hypotheses to determine their validity; and entering said Evaluations of Hypotheses into said computer database;

wherein said patient and said therapist may simultaneously access said computer database during psychotherapy.

7. A computer-assisted process for interactive psychotherapy, comprising the steps of:

providing conventional talk therapy from a psychotherapist to a patient;

entering data from said talk therapy into a computer database comprising a plurality of interrelated sub-databases;

reviewing said data entered into said computer database as a part of said talk therapy;

sorting, manipulating, and examining said data on said computer database to derive information regarding said talk therapy from said data in said computer;

providing a plurality of input/output devices for said computer to access said computer database; and having said patient and said psychotherapist simultaneously access said computer database via said input/output devices during a talk therapy session;

wherein said data on said computer database is manipulable by both said psychotherapist and said patient.

8. The process of claim 7, further comprising the steps of:

accessing said data in said computer database; and examining and manipulating said data from said talk therapy to sort said data into categories including Empirical Data, Historical Data, and Dreams.

9. The process of claim 8, wherein said step of deriving information further comprises the steps of:

accessing said data in said computer database;

sorting, manipulating, and examining said Empirical Data, Historical Data, and Dreams in said computer database to identify patterns therein;

formulating Generalizations based on said patterns in said Empirical Data, Historical Data, and Dreams; and entering said Generalizations into said computer database.

10. The process of claim 9, wherein said step of deriving information further comprises the steps of:

formulating Hypotheses as proposed explanations of said Generalizations; and entering said Hypotheses into said computer database.

11. The process of claim 10, wherein said step of deriving information further comprises the steps of:

formulating patient Goals based on said Generalizations; and entering said Goals into said computer database.

12. The process of claim 11, wherein said step of deriving information further comprises the steps of:

formulating Actions to accomplish said Goals, based on said Hypotheses; and entering said Actions into said computer database.

13. The process of claim 11, wherein said step of deriving information further comprises the steps of:

accessing said Goals on said computer database;

evaluating to what extent said Goals have been accomplished to determine the progress said patient has make in said psychotherapy; and entering said Evaluations of Goals into said computer database.

14. The process of claim 10, wherein said step of deriving information further comprises the steps of:

accessing said Hypotheses in said computer database;

evaluating said Hypotheses to determine their validity; and entering said Evaluations of Hypotheses into said computer database.

15. The process of claim 7, further comprising the step of:

accessing said data in said computer database; and examining and manipulating said data to sort said data according to importance.

16. The process of claim 7, wherein said process is implemented in an apparatus comprising:

at least one computer, being either a personal computer, mainframe computer or networked computer;

an interactive database operably accessible by said computer;

a program stored in said computer for directing use of, and access to, said database;

display means in communication with said computer and arranged for simultaneous viewing by a psychotherapist and by a patient; and data entry means in communication with said interactive database and arranged for simultaneous use by said psychotherapist and said patient;

wherein said interactive database is available for simultaneous, real time use during psychotherapy by said psychotherapist and said patient.

17. The process of claim 7, wherein said process is implemented in the apparatus of claim 16, and wherein said display means is selected from the group consisting of flat screen (LCD) displays, individual video monitors, projection video, and large screen display.

18. The process of claim 7, wherein said process is implemented in the apparatus of claim 16, and wherein said data entry means is a keyboard.

* * * * *